US010932981B2

(12) United States Patent
Bratic et al.

(10) Patent No.: US 10,932,981 B2
(45) Date of Patent: Mar. 2, 2021

(54) VERTEBRAL DECOMPRESSION DEVICE (71) Applicant: JAPET MEDICAL DEVICES, Lille (FR)

(72) Inventors: Damien Bratic, Paris (FR); Antoine Noel, Aubry du Hainaut (FR)

(73) Assignee: Japet Medical Devices, Lille (FR)

(*) Notice: Subject to any disclaimer, the term of this patent is extended or adjusted under 35 U.S.C. 154(b) by 406 days.

(21) Appl. No.: 15/567,651

(22) PCT Filed: Apr. 8, 2016

(86) PCT No.: PCT/FR2016/050810
§ 371 (c)(1),
(2) Date: Oct. 19, 2017

(87) PCT Pub. No.: WO2016/170244
PCT Pub. Date: Oct. 27, 2016

(65) Prior Publication Data
US 2018/0085279 A1  Mar. 29, 2018

(30) Foreign Application Priority Data
Apr. 20, 2015 (FR) ...................... 15 53515

(51) Int. Cl.
A61F 5/02 (2006.01)
A61H 1/02 (2006.01)

(52) U.S. Cl.
CPC .......... A61H 1/0292 (2013.01); A61F 5/028 (2013.01); A61H 2201/123 (2013.01);
(Continued)

(58) Field of Classification Search
CPC . A61F 5/028; A61H 1/0292; A61H 2201/123; A61H 2201/5061; A61H 2201/5064; A61H 2201/5097
See application file for complete search history.

(56) References Cited

U.S. PATENT DOCUMENTS 1,589,670 A * 6/1926 Vartia .................. A61F 5/024
602/36
2,886,031 A * 5/1959 Robbins .............. A61F 5/024
602/19
4,715,362 A * 12/1987 Scott .................. A61F 5/024
602/19

(Continued)

FOREIGN PATENT DOCUMENTS

EP      0319224 B1    2/1992

OTHER PUBLICATIONS

Australian Government IP Australia Examination Report No. 1, dated Nov. 8, 2019, 4 pages, for Application No. 2016252083 Japet Medical Devices Apr. 20, 2015.
(Continued)

Primary Examiner — Kim M Lewis
(74) Attorney, Agent, or Firm — Fay Sharpe LLP (57) ABSTRACT A vertebral decompression device (10) configured to surround a user's trunk, the device comprising: upper support means (12) configured to surround a first portion of the trunk; lower support means (14) configured to surround a second portion of the trunk; and elongation means (16) mounted on the upper support means (12) and the lower support means (14) and configured to exert a separating force on the lower and upper support means tending to move the lower support means away from the upper support means. The device further includes an electronic control system (18) for controlling the elongation means (16) in such a manner as to maintain a determined distraction force on the user's vertebral column.

13 Claims, 4 Drawing Sheets (52) U.S. Cl.
CPC ............... *A61H 2201/5061* (2013.01); *A61H 2201/5064* (2013.01); *A61H 2201/5097* (2013.01)

(56) References Cited

U.S. PATENT DOCUMENTS

| | | | | |
|---|---|---|---|---|
| 4,721,102 A * | 1/1988 | Pethybridge | ............ | A61F 5/024 602/19 |
| 5,462,518 A * | 10/1995 | Hatley | ............ | A61F 5/024 482/124 |
| 5,651,764 A | 7/1997 | Chiu | | |
| 5,916,188 A * | 6/1999 | Ousdal | ............ | A61F 5/055 602/32 |
| 6,210,354 B1 * | 4/2001 | Ousdal | ............ | A61F 5/055 602/36 |
| 6,997,892 B2 * | 2/2006 | Reinecke | ............ | A61F 5/024 602/19 |
| 7,445,608 B2 * | 11/2008 | Dunfee | ............ | A61F 5/024 128/845 |
| 7,591,797 B2 | 9/2009 | Hakonson | | |
| 9,987,159 B2 * | 6/2018 | Williams | ............ | A61F 5/026 |
| 2004/0077982 A1 | 4/2004 | Reinecke | | |
| 2009/0036888 A1 | 2/2009 | Dunfee et al. | | |
| 2009/0292230 A1 * | 11/2009 | Anquetil | ............ | A61F 5/028 602/19 |
| 2013/0345612 A1 * | 12/2013 | Bannister | ............ | A61B 5/1116 602/19 |
| 2014/0039371 A1 * | 2/2014 | Johnson | ............ | A61F 5/02 602/19 |
| 2014/0276308 A1 * | 9/2014 | DiAngelo | ............ | A61F 5/03 602/19 |
| 2014/0364784 A1 | 12/2014 | Hyde | | |

OTHER PUBLICATIONS

European Examination Notification for Application No. 16 733 124.8, dated Aug. 3, 2020 (dated Aug. 3, 2020).

* cited by examiner

VERTEBRAL DECOMPRESSION DEVICE

BACKGROUND OF THE DISCLOSURE

The present disclosure provides a vertebral decompression device. It finds a particular application in relieving people suffering from back pain, e.g. caused by a herniated disk. Such pains arise, amongst other reasons, because the vertebrae are excessively compressing the intervertebral disks that separate them from one another.

Relief may be obtained by exerting a distraction force on the vertebral column so as to decoapt the vertebrae. The term "decoaptation" is used to mean increasing the inter-joint space between two surfaces that are too close together.

Vertebral decompression devices are known that enable a distraction force to be exerted on the user's vertebral column.

By way of example, one such device is proposed in Document EP 0 319 224, which describes a vertebral decompression device configured to surround a portion of the user's trunk, the device comprising an upper support, a lower support, and two telescopic bars mounted on the lower and upper supports so as to exert a separating force on the lower and upper supports.

Each telescopic bar includes an actuator lever suitable for enabling a third party, such as a health professional, to move the lower and upper supports apart from each other while the device is being worn by the user, thereby exerting a distraction force on the user's vertebral column.

Nevertheless, such a device is particularly bulky and in particular it cannot be worn under clothing. In addition, it significantly reduces the user's mobility, such that it cannot be worn for more than a few minutes. Furthermore, it needs to be installed and actuated with the help of a third party. Nor does it make it possible to adapt the separating force exerted by the telescopic arms, e.g. as a function of the movements performed by the user, such that the distraction force varies, e.g. while the user is moving, which tends to limit the relief given by the device.

OBJECT AND SUMMARY OF THE DISCLOSURE

Amongst others, the present disclosure has the object of resolving the above-described insufficiencies of vertebral decompression devices known in the prior art by proposing a vertebral decompression device that the user can put on alone and that can be worn all day in a manner that is discreet and effective, with the magnitude of the distraction force applied to the vertebral column being constant independently of the position or the movements of the user.

This object is achieved by a vertebral decompression device configured to surround a user's trunk, the device comprising upper support means configured to surround a first portion of the trunk, lower support means configured to surround a second portion of the trunk, and elongation means mounted on the upper support means and the lower support means and configured to exert a separating force on the lower and upper support means tending to move the lower support means away from the upper support means; in addition, the device includes an electronic control system for controlling the elongation means in such a manner as to maintain a determined distraction force on the user's vertebral column.

When considered with the user in a substantially vertical position, the second portion of the trunk is located under the first portion of the trunk.

Because of the presence of the electronic control system, the user can make use of the device unaided. In addition, by maintaining a determined distraction force, the effectiveness of the device is improved, with the relief from which the user benefits not varying, in particular as a function of the user's movements and/or positions.

The elongation means may include a power supply such as a battery enabling them to be actuated without external assistance.

The disclosure is set out below in a series of variant embodiments that may be considered singly or in combination with one or more of the preceding variant embodiments.

The electronic control system may include regulator means for modifying the magnitude of the distraction force.

By this provision, the device, and more particularly the magnitude of the distraction force on the user's vertebral column, are adapted to relieving users who may present differing morphologies or who may suffer from pains of different magnitudes, for example. In addition, the presence of the adjustment means enable the device to be adapted to changes in the user's condition.

The vertebral decompression device may include measurement means configured to measure at least one characteristic relating to the movements of the user.

The electronic control system may be configured to modify the separating force exerted by the elongation means as a function of the measurements taken by the measurement means.

Thus, the value and/or the direction of the separating force can also be modified as a function of the characteristics of the user as measured by the measurement means, so that the magnitude of the distraction force is constant, e.g. independently of the movements of the user.

The electronic control system may be configured to modify the magnitude of the distraction force as a function of the measurements taken by the measurement means.

It can thus be understood that the adjustment means are configured to modify the magnitude of the distraction force as a function of the user's mobility or position.

The vertebral decompression device may further include recording means for recording the measurements taken by the measurement means.

The recording means thus serve to store some or all of the user's movements and the positions during the period the user is wearing the device, e.g. so as to identify behaviors that might give rise to or contribute to the user's back pain.

The elongation means may comprise at least one linear actuator.

By this provision, the compactness, the lightness, and consequently the comfort in use of the device are not compromised. In addition, the accuracy of the separating force exerted by the elongation means in terms both of value and of direction, and consequently the effectiveness of the device in relieving the pain felt by the user are likewise improved.

At least one linear actuator may be hinge-mounted relative to the upper support means and/or to the lower support means.

By this provision, the freedom of movement of the user is not compromised while wearing the device of the present disclosure. It is thus easy for the user to move or, by way of example, to bend the upper portion of the body relative to the lower portion, where such behaviors are significantly limited, if not impossible, with known devices of the prior art.

The electronic control system may be configured to limit the movements of said at least one linear actuator relative to the upper support means and/or to the lower support means.

By this provision, the user is prevented from performing such movements that run the risk of injuring the user or increasing the pain felt.

The elongation means may comprise at least first and second linear actuators configured to lie on opposite sides of the trunk when the device is worn by the user.

The presence of two linear actuators on opposite sides of the user's trunk serves to distribute the separating force exerted by the elongation means better over the lower and upper support means, thereby increasing the effectiveness of the device, without compromising the mobility of the user.

The elongation means may comprise two pairs of linear actuators configured to extend on opposite sides of the trunk while the device is being worn by the user.

By this provision, the separating force exerted by the elongation means is still better distributed over the user's trunk. In addition, it provides the user wearing the device of the present disclosure with better mobility and further increases the effectiveness of the device.

The linear actuators in a given pair may be inclined relative to each other so as to further increase the freedom of movement of the user when wearing the vertebral decompression device of the present disclosure, while still making it possible, because of the presence of the electronic control system, to prevent the user from performing certain movements that run the risk of being painful to the user.

The linear actuators in a given pair may be in a V-arrangement.

The tip of the V-shape formed by the linear actuators in a given pair may point downwards.

Each linear actuator may extend in a direction that is inclined relative to the axis of the vertebral column.

The linear actuators of the elongation means may be configured to exert separating forces of value and direction that are different.

This provision enables the distraction force to be better distributed over the vertebral column so as to increase the effectiveness of the device of the present disclosure.

The upper and lower support means may be configured to surround respectively an upper portion and a lower portion of the lumbar segment of the user's vertebral column.

The upper and lower support means may be configured to be adjusted around the trunk portion they surround.

The upper and lower support means may include an adjustable belt configured to adapt the device to different user morphologies.

The upper and lower support means may be substantially conical in shape so as to increase the stability with which the device is fastened on the user's trunk, and consequently increase the accuracy, in terms of positioning and magnitude, of the distraction force that it applies to the user's vertebral column.

Embodiments of the present disclosure also provide a vertebral decompression system comprising a vertebral decompression device of the present disclosure and a data processor system, the electronic control system of the vertebral decompression device further comprising wireless transmission means configured to transmit the measurements taken by the measurement means to the processor system.

By this provision, the system is configured to enable data to be exchanged between the user and a third party, such as a health professional, so as to adjust the prescription relating to the conditions of use of the device, such as the magnitude of the distraction force.

The wireless transmission means may be configured to transmit data relating to the elongation means to the data processor system, which data may comprise variations in the value and/or the direction of the separating force.

The wireless transmission means may be configured to transmit the data recorded by the recording means to the processor system.

By this provision, the processor system can process data relating to a significant period of use of the device of the present disclosure.

The processor system may include a storage device configured to store the data transmitted by the wireless transmission means of the electronic control system.

Thus, during successive exchanges of data with the device, a third party can compare the received data, e.g. so as to evaluate the effectiveness of changes in the parameters that are applied.

BRIEF DESCRIPTION OF THE DRAWINGS

Other characteristics and advantages of the disclosure appear more clearly and more completely on reading the following description of an embodiment given by way of non-limiting example and with reference to the following accompanying drawings, in which.

DETAILED DESCRIPTION

In the embodiment shown in FIGS. 1 to 3, the vertebral decompression device 10 of the present disclosure comprises upper support means 12, lower support means 14, and elongation means 16 that, as described in greater detail below in the description, are mounted both on the upper support means 12 and on the lower support means 14, the elongation means 16 being configured to exert a separating force on the lower and upper support means 14 and 12, tending to move the lower support means 14 away from the upper support means 12.

The vertebral decompression device 10 also includes an electronic control system 18 that is fastened by way of non-limiting example on the upper support means 12.

The device 10 also includes measurement means 20 and recording means 22 that are described in greater detail below.

The upper support means 12 and the lower support means 14 include various textile portions 24, 26, 28, 30 that are connected together by way of non-limiting example by elastic tapes 32, 34 configured to adapt the upper and lower support means 12, 14 to fit the morphology of the user.

In addition, the upper and lower support means present closure means 36, 38, specifically clip-fastenable straps for making it easier to put the device on a user.

Figure 1:
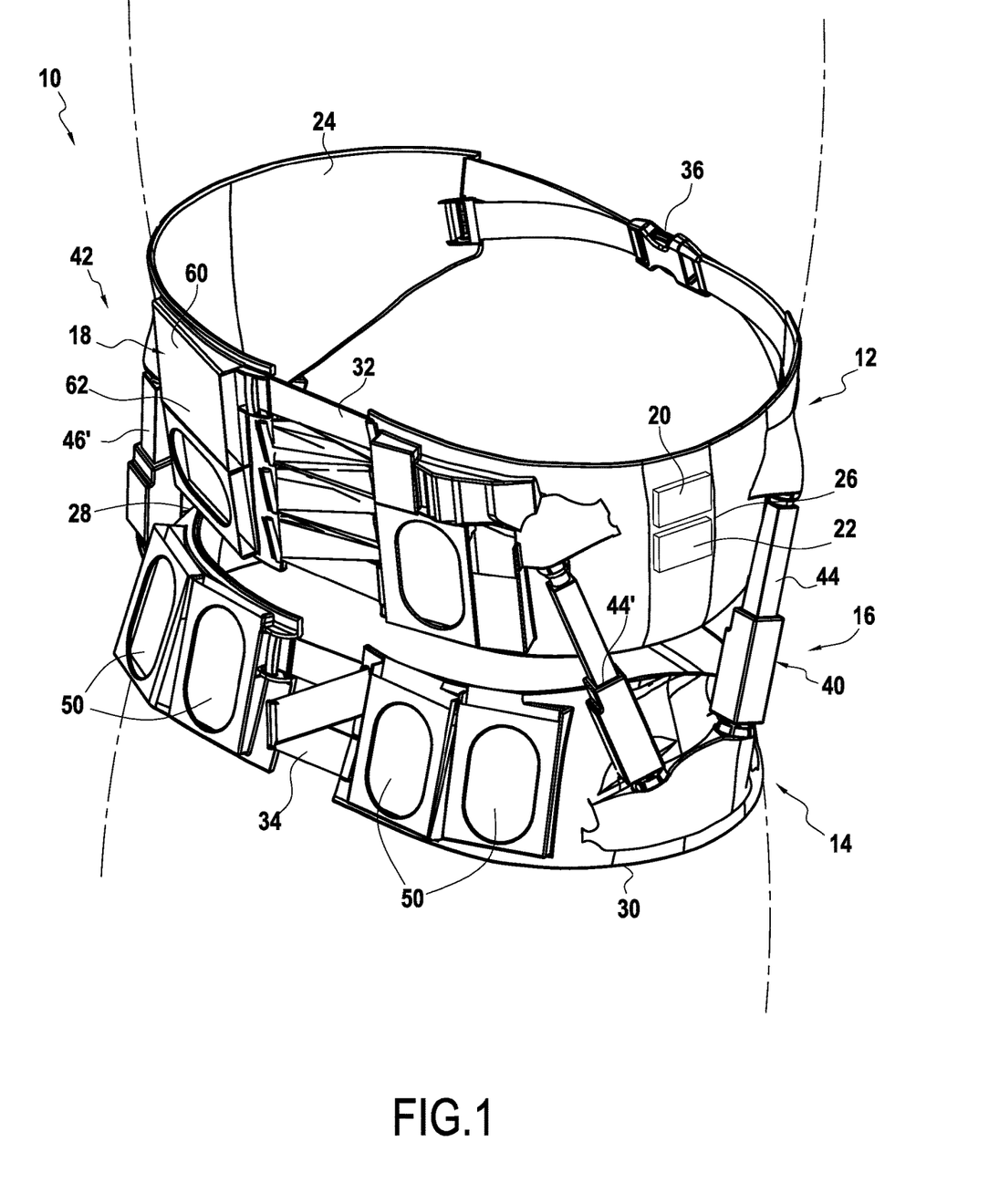
FIGS. 1 and 2 are diagrams showing an example of a vertebral decompression device according to embodiments of the disclosure, seen respectively from behind and from in front.
Figure 2:
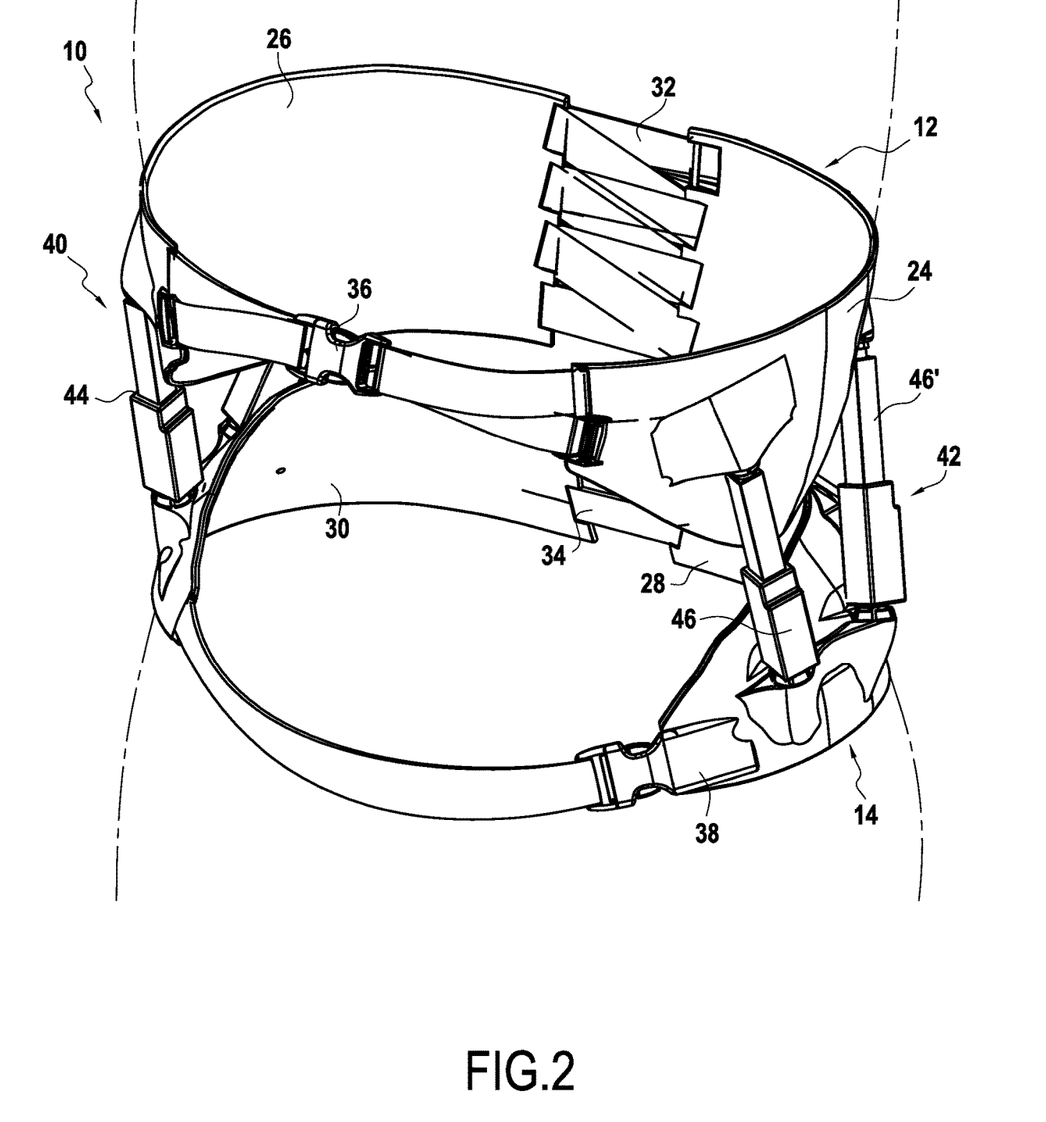
Figure 3:
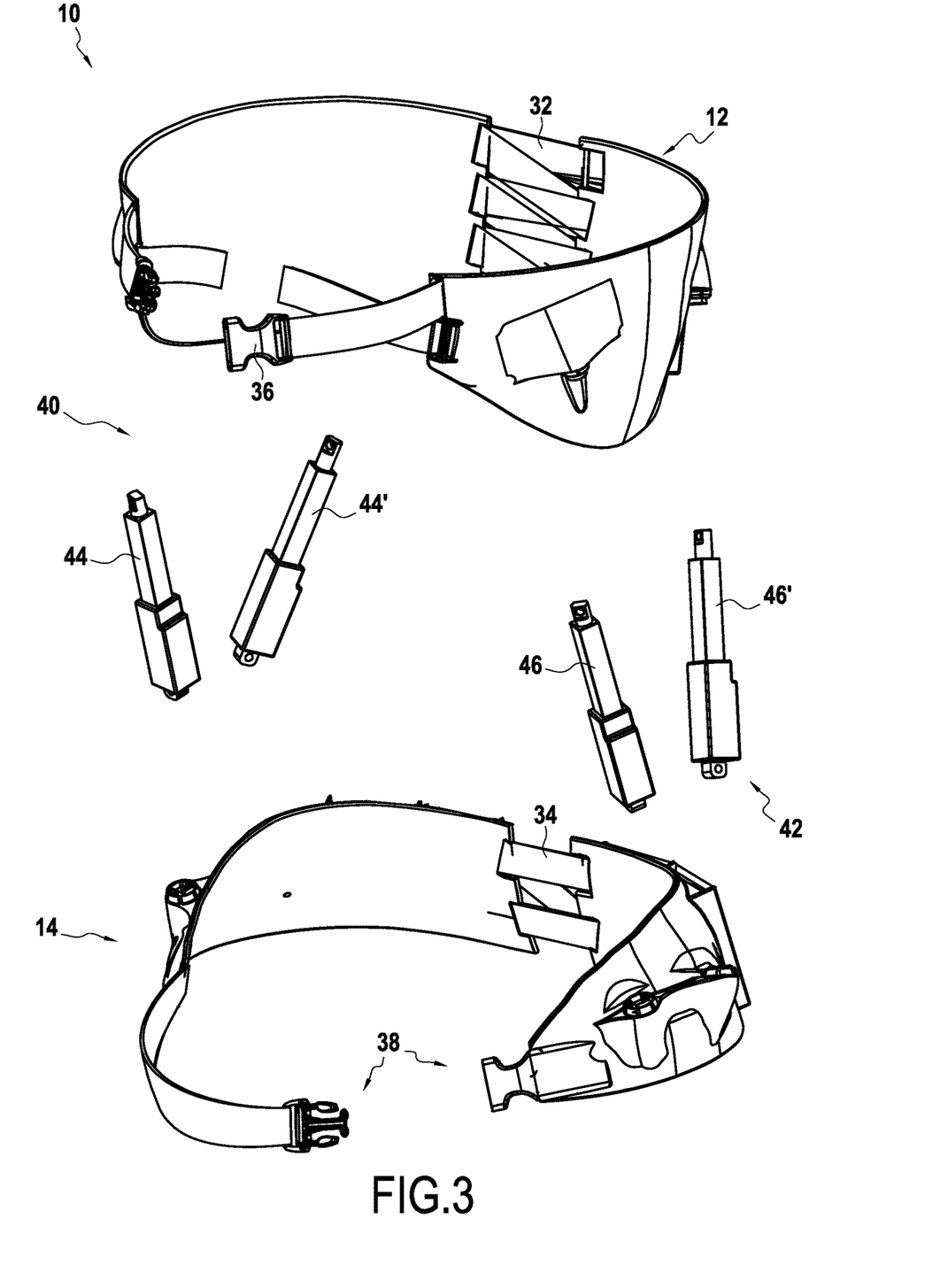
FIG. 3 is a partially exploded diagrammatic view of the device of the present disclosure.

In particular, FIGS. 1 and 2 show the device 10 worn by a user, with the user's silhouette being represented by chain-dotted lines.

The upper support means 12 thus present the form of a belt configured to surround a first portion of a user's trunk; by way of non-limiting example, the upper support means 12 are configured to surround the middle portion of the user's torso.

The lower support means 14 are also in the form of a belt configured to surround a second portion of the user's trunk, and by way of non-limiting example a portion of the user's abdominal girdle.

It can thus be understood that the upper and lower support means 12 and 14 are configured to surround a portion of the user's vertebral column, and by way of non-limiting example the lumbar segment of the vertebral column.

By way of non-limiting example, the lower and upper support means 14 and 12 are made of a material presenting non-allergenic properties; by way of example, they may also be coated in thermoformable foam so as to enable the vertebral decompression device 10 to be fitted better to the user's morphology and improve co-operation between the support means 12, 14 and the user's trunk.

By way of non-limiting example, the upper and lower support means 12 and 14 are conical in shape, being configured to further improve the co-operation of the lower and upper support means 14 and 12 with the user's trunk.

As shown in the various figures, the elongation means 16 comprise first and second pairs 40 and 42 of elongation actuators, the first and second pairs 40, 42 being configured to lie on opposite sides of the trunk, when the device 10 is worn by the user.

By way of non-limiting example, each of the pairs 40 and 42 comprises a first and a second linear actuator 44, 44', 46, 46'. By way of non-limiting example, the various linear actuators 44, 44', 46, 46' are electric actuators; without going beyond the ambit of the present disclosure, it would naturally be possible to devise any other type of linear actuator, such as for example a hydraulic actuator.

Each of the actuators presents a longitudinal direction and first and second mutually opposite ends; as shown in particular in FIGS. 1 and 2, one of the ends of each linear actuator is mounted on the upper support means 12, while its other end is mounted on the lower support means 14.

By way of non-limiting example, the linear actuators 44, 44', 46, 46' include ball joints mounted at each of their ends and configured so that the various linear actuators are hinged relative to the upper support means 12 and to the lower support means 14.

As shown in the various figures, the linear actuators are mounted by means of pockets formed on the upper and lower support means 12 and 14, and more particularly on their textile portions 24, 26, 28, and 30, the ends of the various linear actuators being received in said pockets; without going beyond the ambit of the present disclosure, it would naturally be possible to devise any other means for mounting linear actuators on the support means 12, 14.

The elongation means 16 also include batteries 50 mounted by way of non-limiting example on the rear portions of the upper and lower support means 12 and 14.

The term "rear" portion is used to mean the portion of the vertebral decompression device 10 that is configured to cover a portion of the user's back while the device 10 is being worn.

The batteries 50 are configured so as to actuate the linear actuators; without going beyond the ambit of the present disclosure, it is possible to devise any other source of power enabling the linear actuators to be actuated without external assistance.

The linear actuators are configured to exert a separating force on the upper and lower support means 12 and 14, with the action of such a separating force serving, to apply a distraction force on the user's vertebral column as a result of the upper and lower support means 12, 14 being secured to the portions of the user's trunk, by moving the lower support means 14 away from the upper support means 12.

The electronic control system 18 of the device 10 is configured to control the elongation means 16 so as to maintain a determined distraction force on the user's vertebral column.

By way of non-limiting example, the electronic control system 18 comprises an electronic board serving to control the value and/or the direction of the separating force exerted by the linear actuators 44, 44', 46, 46'.

In other words, the electronic control system 18 of the device 10 is configured to control the elongation means 16 so as to adjust the separating force that the linear actuators 44, 44', 46, 46' exert on the lower and upper support means; the term "regulation" is used to mean varying the value of the separating force and/or varying the direction in which said separating force is applied.

The measurement means 20 are configured to measure at least one characteristic relating to the movements of the user, such as the user's position, movements of the body as a whole, or relative movements between different portions of the body; by way of non-limiting example, the measurement means 20 include an accelerometer, a gyro, or any other sensor serving to detect the relative positions of different portions of the user.

The electronic control system 18 is also configured to modify the value and/or the direction of the separating force exerted by the linear actuators of the elongation means 16 as a function of the measurements taken by the measurement means 20.

For example, when the user performs walking movements, the magnitude of the distraction force that ought to be applied to the user's vertebral column varies; the electronic control system 18 thus enables the value and/or the direction of the separating force exerted by the various linear actuators 44, 44', 46, 46' to be adjusted in order to take account of the variation in the magnitude of the distraction force.

The recording means 22 are configured to record the measurements taken by the measurement means 20. By way of example, such recording of measurements is particularly useful for enabling a health professional to adapt the magnitude of the distraction force that is to be applied to the user's vertebral column, to adapt the prescription concerning wearing the device, or indeed to give the user advice about movements and/or positions that run the risk(s) of increasing the pain felt and/or of delaying healing.

As shown in the various figures, the first and second pairs 40, 42 of linear actuators are each V-shaped, the longitudinal direction of each of the linear actuators being inclined relative to the axis of the vertebral column.

Amongst other things, this arrangement serves to distribute the force exerted by the linear actuators better without impeding the freedom of movement of the user wearing the device 10.

It can thus be understood that the vertebral decompression device 10 enables a determined distraction force to be maintained on the user's vertebral column, but without that comprising the user's mobility. Thus, the vertebral decompression device 10 of the present disclosure constitutes an exoskeleton serving to support a portion of the user's back.

The electronic control system 18 of the device 10 is also configured to limit the movements of the linear actuators 44, 44', 46, 46' relative to the upper and lower support means 12, 14 so that the user cannot perform movements that might lead to injury or increased pain.

The device 10 of the present disclosure is compact, such that it can be worn quite discreetly under the user's ordinary clothing.

In addition, it provides the user with significant freedom of movement, and in particular because of the above-described batteries 50, it presents a battery life that enables it to be worn for several hours.

In order to further increase the battery life of the device 10, and without going beyond the ambit of the present disclosure, it is possible to devise elongation means 16 comprising semi-active actuators, such as linear actuators co-operating with springs, where such semi-active actuators make it possible to store some or all of the energy released by certain movements of the user and to reuse the stored energy during other movements made by the user.

The electronic control system 18 also includes adjustment means 60 for modifying the magnitude of the distraction force applied to the user's vertebral column by the separating force of the elongation means 16. The adjustment means 60 are thus configured to enable a health professional to match the adjustment of the device 10 to the user's morphology and sensations of pain.

Furthermore, the electronic control system 18 includes wireless transmission means 62 making it possible, amongst other things, to transmit the measurements taken by the measurement means 20.

Without going beyond the ambit of the present disclosure, it is thus possible to devise wireless transmission means 62 that are configured to transmit the variations in the values of the separating force exerted by the elongation means 16 while the device 10 is in use.

Figure 4:
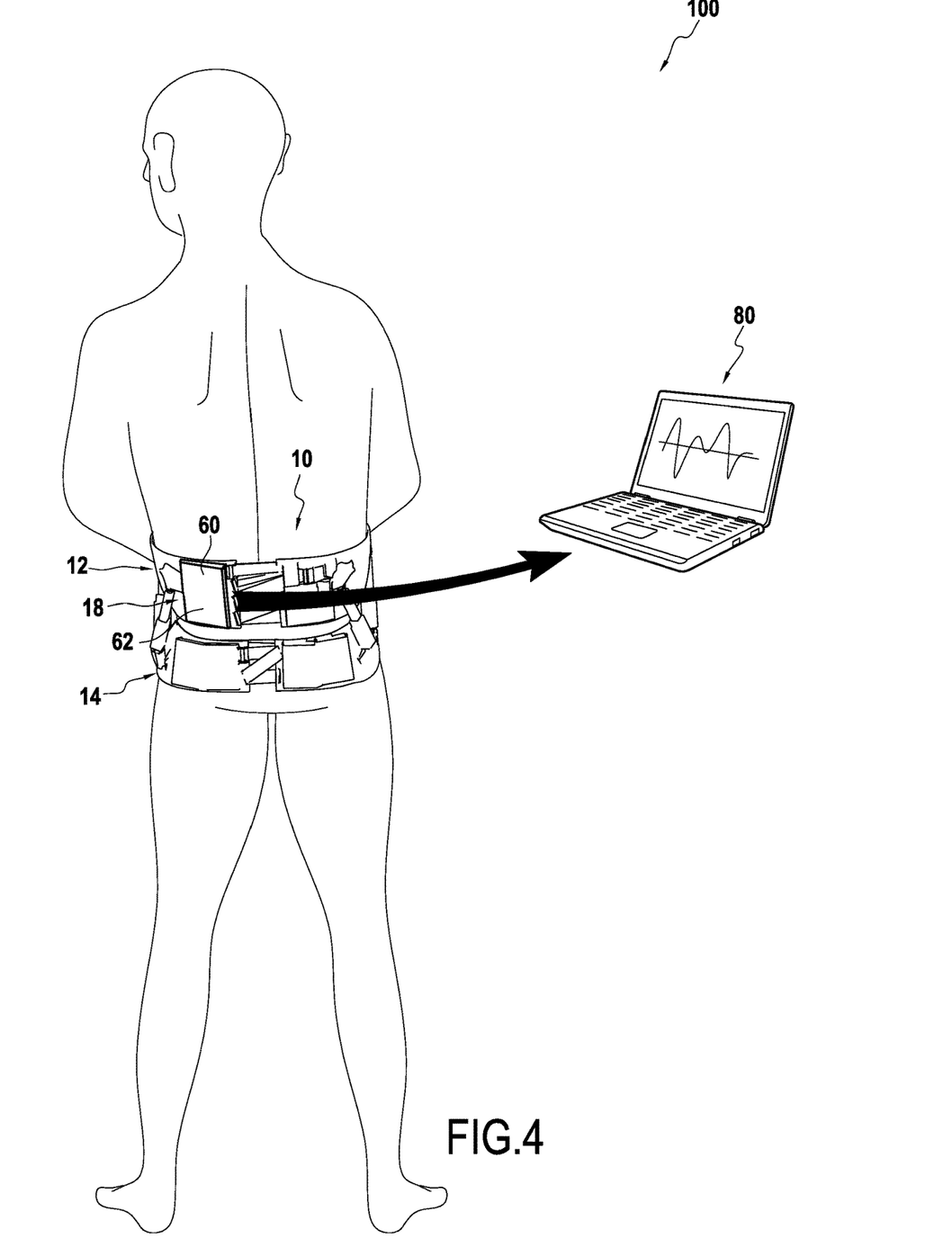
FIG. 4 is a diagram showing a vertebral decompression system of the present disclosure.

The disclosure also relates to a vertebral decompression system 100 including a vertebral decompression device 10 of the present disclosure together with a data processor system 80, e.g. installed in a computer device such as a personal computer or a smartphone, the data processor system 80 being configured to receive the data transmitted by the wireless transmission means 62 of the electronic control system 18.

The vertebral decompression system thus enables a third party, such as a health professional, to access the user's data without it being necessary for the user to take the device 10 off, or even to be close to the third party.

By way of non-limiting example, the wireless transmission means 62 are configured to transmit to the data processor system 80 the data relating to the elongation means 16, such as variations in the value and/or the direction of the separating force.

The wireless transmission means 62 are also configured to transmit to the data processor system 80 the data that has been recorded by the recording means 22; it is also possible to devise a storage device in the data processor system 80 that is configured to store the data that is transmitted by the wireless transmission means 62 of the electronic control system 18 within the vertebral decompression device 10.

The above description is given by way of example, and is therefore not limiting on embodiments of the disclosure.

In particular, although the disclosure is particularly adapted to lumbar pain, it may also be adapted to relieving any other type of back pain, such as cervical pain or chest pain.

In addition, the number, the structure, and the arrangement of the linear actuators of the elongation means of the present disclosure are not limiting in any way on embodiments of the present disclosure.

The invention claimed is:

1. A vertebral decompression device configured to surround a user's trunk, the vertebral decompression device comprising:
   an upper support device configured to surround a first portion of the trunk;
   a lower support device configured to surround a second portion of the trunk; and
   an elongation device mounted on the upper support device and the lower support device and configured to exert a separating force on the lower and upper support device tending to move the lower support device away from the upper support device;
   wherein the vertebral decompression device further includes an electronic control system for controlling the elongation device in such a manner as to maintain a determined distraction force on the user's vertebral column,
   wherein the elongation device comprises two pairs of actuators, configured to extend on opposite sides of the trunk while the vertebral decompression device is being worn by the user,
   wherein the actuators in a given pair are inclined relative to each other;
   wherein the actuators in a given pair are in a V-arrangement, and
   wherein a tip of the V-arrangement points downward.

2. The vertebral decompression device according to claim 1, wherein the electronic control system includes a processor for controlling the magnitude of the distraction force.

3. The vertebral decompression device according to claim 1, further including a measurement device configured to measure at least one characteristic relating to the movements of the user.

4. The vertebral decompression device according to claim 3, wherein the electronic control system is configured to control the separating force exerted by the elongation device as a function of the measurements taken by the measurement device.

5. The vertebral decompression device according to claim 3, further including a memory for recording the measurements taken by the measurement device.

6. The vertebral decompression device of claim 3, wherein said measurement device comprises one of an accelerometer, a gyro, or any other sensor which serves to detect the relative positions of different portions of the user.

7. The vertebral decompression device according to claim 1, wherein the actuators of the elongation device are linear actuators.

8. The vertebral decompression device according to claim 7, wherein said at least one linear actuator is hinge-mounted relative to the upper support device and/or to the lower support device.

9. The vertebral decompression device according to claim 8, wherein the electronic control system is configured to limit the movements of said at least one linear actuator relative to the upper support device and/or to the lower support device.

10. The vertebral decompression device according to claim 1, wherein each actuator extends in a direction that is inclined relative to the axis of the vertebral column.

11. The vertebral decompression device according to claim 1, wherein the actuators are configured to exert separating forces of value and direction that are different.

12. The vertebral decompression device of claim 1, wherein said electronic control system comprises an electronic board.

13. The vertebral decompression system of claim 1, wherein said electronic control system comprises a wireless transmission device comprising Bluetooth or WiFi.

\* \* \* \* \*